United States Patent [19]
Bledsoe, Jr. et al.

[11] 4,204,080
[45] May 20, 1980

[54] HYDROGENATION PROCESS FOR THE SELECTIVE PREPARATION OF 3-MENTHENE

[75] Inventors: James O. Bledsoe, Jr.; Carlos G. Cardenas, both of Jacksonville, Fla.

[73] Assignee: SCM Corporation, New York, N.Y.

[21] Appl. No.: 5,138

[22] Filed: Jan. 22, 1979

[51] Int. Cl.² ........................... C07C 5/06; C07C 5/30; B01J 23/46
[52] U.S. Cl. .................... 585/273; 585/350; 585/947
[58] Field of Search .................. 585/947, 350, 273

[56] References Cited

U.S. PATENT DOCUMENTS 3,804,914  4/1974  Fahey ................................ 585/273
3,925,494  12/1975  Fahey ................................ 585/273

OTHER PUBLICATIONS

Darryl R. Fahey "Selective Hydrogenation Catalyzed by Ruthenium Complexes" J. Organic Chem. 38, 80–89, 3343–3348 (1973).

Primary Examiner—Delbert E. Gantz
Assistant Examiner—G. E. Schmitkons
Attorney, Agent, or Firm—Merton H. Douthitt; Jerry K. Mueller, Jr.

[57] ABSTRACT

Non-conjugated para-menthadienes having one site of unsaturation at the 4(8)- or 8-position are hydrogenated to selectively form 3-menthene in the presence of a homogeneous ruthenium catalyst complex.

10 Claims, No Drawings

HYDROGENATION PROCESS FOR THE SELECTIVE PREPARATION OF 3-MENTHENE

BACKGROUND OF THE INVENTION

The present invention relates to a novel process for the preparation of 3-menthene and more particularly to a novel selective hydrogenation process utilizing a homogeneous ruthenium catalyst complex therefor.

Fahey reports that cyclic polyenes can be hydrogenated to selectively form cyclic monoenes in the presence of certain ruthenium (II) catalyst complexes (see U.S. Pat. Nos. 3,804,914 and 3,925,494; *JOC*, Vol. 38, pages 80–87 and 3343–3348, 1973; and *Catalysis in Organic Synthesis*—1976, Acad. Press, pages 287–304). Of particular interest to Fahey is the selective hydrogenation of 1,5,9-cyclododecatriene for forming cyclododecene.

The present invention is based on the discovery that homogeneous ruthenium (II) catalyst complexes can catalyze the hydrogenation of specific paramenthadienes to selectively form 3-menthene which is valuable intermediate in the synthesis of menthol, for example. Such selective hydrogenation process for the formation of 3-menthene is suprising since it is well known that conventional catalytic hydrogenation of such para-menthadienes using, for example, nickel or palladium catalysts, produces predominantly 1-menthene or 2-menthene which then must be isomerized to 3-menthene.

BRIEF SUMMARY OF THE INVENTION

The present invention is a process for catalytically hydrogenating a nonconjugated para-menthadiene having one site of unsaturation at the 8-position or the 4(8)-position, for selectively forming 1-methyl-4-isopropylcyclohex-3-ene (3-menthene). Such process comprises contacting with hydrogen gas under hydrogenation conditions a reaction mixture comprising said para-menthadiene, a catalytic proportion of a ruthenium (II) catalyst complex, and an organic solvent in which said catalyst complex is soluble or homogeneously dispersed, until said 3-menthene is formed. Such catalyst complex is restricted to one which is capable of catalyzing a selective hydrogenation of a cyclic polyene to a cyclic monoene. Preferably, the organic solvent is an amide solvent or a lactam solvent.

DETAILED DESCRIPTION OF THE INVENTION

The ruthenium (II) catalyst complexes which are capable of selectively hydrogenating a cyclic polyene to a cyclic monoene are shown, for example, by Fahey in the citations given above. The disclosures of said citations are expressly incorporated herein by reference. The preferable ruthenium (II) catalyst complexes for use in the present invention contain phosphine ligands and can be represented conventionally by the following general formula:

where
X is a halogen or a hydrogen atom,
a is 0, 1, or 2,
b is 2 or 3,
a+b is 3 or 4,
L is $PR_3$ or $R_2P-R'-PR_2$, where R and R' are aliphatic, aromatic, or aliphatic-aromatic radicals, and advantageously where R is an alkyl, aryl, cycloalkyl radical or combinations thereof, and R' is an alkylene or cycloalkylene radical.

A preferred ruthenium (II) catalyst complex for use in the present process can be represented as follows:

$RuCl_2(CO)_2(Ph_3P)_2$, where Ph is a phenyl group.

Such preferred ruthenium (II) catalyst complexes are commercially available or can be synthesized by techniques well known in the art. Alternatively, such ruthenium catalyst complexes can be formed in situ in the reaction mixture during the hydrogenation process, for example, from triphenylphosphine and ruthenium trichloride with or without the presence of carbon monoxide and optionally with a slight excess of triphenylphosphine to ensure that all the ruthenium is in the catalyst complex form during the hydrogenation process. The proportion of ruthenium (II) catalyst complex by weight of the feed para-menthadiene broadly is greater than about 0.05%, and can range from between about 0.05 to about 100%, advantageously between about 0.05 and about 5%, and preferably between aboout 0.1 and about 1%.

The feed for the present process is a non-conjugated (or unconjugated) para-menthadiene containing one site of unsaturation at the 8- or the 4(8)-position. Nomeclature of the various para-menthadienes and related compounds is conventional and is based on the para-menthane carbon skeleton represented conventionally as follows:

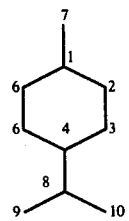

The selective catalytic hydrogenation process appears to involve both a hydrogenation step and an isomerization step since the product 3-menthene contains but a single endocyclic double bond in the 3-4 position of the cyclohexene ring (adjacent the isopropyl group) and feed para-menthadienes have no double bond at this position. That the unsaturation in the product is in such position within the cyclohexene ring indeed is surprising and unique. Preferable menthadienes for use in the present process include, for example, limonene (1,8-menthadiene), terpinolene (1,4(8)-menthadiene), isolimonene (2,8-menthadiene), psi-limonene (1(7),8-menthadiene), 1(7),4(8)-menthadiene, and mixtures thereof. It should be noted that 2,4(8)-menthadiene, 3,8-menthadiene, and various other menthadienes may be included in the feed mixture also. The preferred terpenes can be provided from natural sources (for example, sulfate turpentine) or synthesized by a wide variety of techniques well-known in the art.

The solvent used in the present process can be important and should be selected with care. The appropriate solvent is one which is capable of solvating the ruthenium (II) catalyst complex for forming a homogeneous or soluble ruthenium catalyst complex system. A variety of organic solvents which are suitable for use in the present invention include, for example, benzene, toluene, cumene, iso-octane, tetrahydrofuran, cyclohexane, ethanol, 1-butanol, ethylacetate, and the like. A preferred class of solvents determined for use in the present process comprises amide solvents and lactam solvents, optionally in admixture with conventional organic solvents such as those named above. The most preferable amide solvent is dimethylformamide (DMF), though other amide and lactam solvents such as, for example, dimethylacetamide, N-methylpyrrolidone and the like find utility in the present process. The weight ratio of feed menthadiene to solvent generally is between about 2:1 to about 10:1.

Hydrogenation conditions for carrying out the present process are conventional for hydrogenation processes utilizing the disclosed ruthenium (II) catalyst complexes. Thus, hydrogenation pressures broadly can range from about 0 to 600 psig, advantageously about 80–440 psig, and temperatures broadly can range from about 25° C. to about 225° C., and advantageously between about 100° and 200° C. Reaction times for the present process for selectively forming 3-menthene can vary from an hour or so on up to 60 hours or more depending upon a variety of factors such as, for example, the particular para-menthadiene fed to the process, the proportion of ruthenium (II) catalyst complex used in the process, the particular solvent employed, and the hydrogenation conditions established in the process.

At the completion of the selective hydrogenation process, the product 3-menthene preferably is separated from the reaction mixture by distillation advantageously practiced at reduced pressures of from about 1 to about 300 millimeters of mercury. Product purification is especially convenient and efficient when the preferred DMF solvent is used, because the product 3-menthene is contained in an upper liquid phase substantially distinct from a lower liquid phase of solvent containing the ruthenium (II) catalyst complex. Of course, a variety of other techniques well known in the art can be used for separating the product 3-menthene from the reaction mixture at the conclusion of the selective hydrogenation process. The distillation residue or lower phase comprising solvent and catalyst can be reused in the process optionally with additional make-up fresh catalyst and/or solvent added thereto.

For present purposes, the present invention is judged to be selective in the formation of product 3-menthene when a preponderance of 3-menthene over all other para-menthenes (chiefly 1-menthene usually) is contained in the product reaction mixture. Typically, the reaction mixxtue will contain about 60% to 70% by weight or more of the desired 3-menthene at the conclusion of the present process. Also, a valuable feature of the present process is the production of optically active 3-menthene from optically active iso-limonene fed to the present process.

The following examples show in detail how the present invention can be practiced but should not be construed as limiting. In this application, all percentages and proportions are by weight and all units are in the metric system, unless otherwise expressly indicated.

EXAMPLE 1

Citrus d-limonene (70 g.) was stirred at 160° C. in the presence of dimethylformamide solvent (DMF, 35 ml.) and RuCl$_2$(CO)$_2$(PPh$_3$)$_2$ catalyst (0.7 g.) under a hydrogen pressure of 80–200 psig. Periodic samples were removed from the reaction mixture and analyzed by vapor phase chromatography to give the following results:

Table 1

| Sample | % 3-Menthene | % 1-Menthene | % Limonene | % 4(8)-Menthene | % Terpinolene + 2,4(8)-Menthadienes |
|---|---|---|---|---|---|
| 1 hr. | 50.6 | 11.6 | 10.2 | 10.6 | 13.0 |
| 2 hr. | 62.7 | 17.7 | 1.1 | 13.1 | 2.8 |
| 3 hr. | 61.4 | 21.6 | — | 12.8 | 0.6 |

The foregoing tabulated results clearly demonstrate that a highly selective hydrogenation has taken place.

EXAMPLE 2

Terpinolene (70 g.) was stirred at 160° C. in the presence of dimethylformamide (35 ml.) and RuCl$_2$(CO)$_2$(PPh$_3$)$_2$ catalyst (0.7 g.) under a hydrogen pressure of 340–440 psig. Analysis of the reaction mixture after 1 hour showed the presence of 68.2% 3-menthene, 12.9% 1-menthene, 14.8% 4(8)-menthene and 1.2% terpinolene, and 2,4(8)-menthadiene.

EXAMPLE 3

The reaction product from Example 2 was found to consist of two layers, the lower of which contained DMF solvent and the catalyst (31 g. total). This lower layer was recovered, added to fresh terpinolene, and the selective hydrogenation repeated. This recovery and reuse procedure was repeated three (3) times. The results obtained are as follows:

Table 2

| Run No. | Temp (°C.) | Press (psig) | Time (Hrs.) | % 3-Menthene | % 1-Menthene | % 4(8)-Menthene | % Dienes |
|---|---|---|---|---|---|---|---|
| 1 | 160 | 340 | 1.0 | 67 | 9.9 | 14.4 | 4.4 |
| 2 | 160 | 340 | 1.0 | 66 | 8.5 | 14.0 | 9.0 |
| 3 | 160 | 200 | 2.0 | 62 | 5.2 | 12.9 | 13.9 |
|   |   |   | 4.0 | 70 | 11.6 | 13.6 | 2.2 |

These results show that the ruthenium (II) catalyst complex can be recovered for reuse in the process. Also, the ease of recovery of the product 3-menthene and separation from the catalyst is demonstrated.

EXAMPLE 4

In a 300 ml. Parr bomb were stirred citrus d-limonene (70.0 g.) triphenylphosphine (0.0974 g.), and RuCl$_3$.xH$_2$O (0.0468 g.). The bomb was pressurized with carbon monoxide to 20 psig. and then warmed to 160° C. under stirring to form the ruthenium (II) catalyst complex in situ. The pressure was vented to 10 psig. and then pressurized to 400 psig. with hydrogen, and stirring was continued at 160° C. After 6¼ hours, analysis of the reaction mixture showed the presence of 63.2% 3-menthene, 22.0% 1-menthene, 1.2% limonene, 9.7% 4(8)-menthene and 1.3% terpinolene plus 2,4(8)-menthadiene.

EXAMPLE 5

In a 300 ml. Parr bomb were stirred citrus d-limonene (100 g.) RuCl$_2$(CO)$_2$(PPh$_3$)$_2$ (0.1 g.) and dimethylformamide (20.0 g.). The bomb was pressurized with hydrogen and heated to 160° C. while maintaining a pressure of 100 psig. After 10 hours, the bomb was cooled and vented and the reaction mixture was subjected to distillation (70°–100° C., 100 mm Hg) leaving 1.5 grams of residue. The distillate contained 64% 3-menthene, 14%

1-menthene, 3% limonene, 12% 4(8)-menthene and 4% terpinolene and 2,4(8)-menthadiene. The residue from the distillation was admixed with 20 g. of fresh DMF and transferred to the Parr bomb along with more citrus d-limonene 100.0 g.). Hydrogenation was conducted as before and after 12 hours the reaction mixture again was distilled providing a distillate containing 64% 3-menthene, 15% 1-menthene, 2% limonene, 12% 4(8)-menthene and 4% terpinolene and 2,4(8)-menthadiene. The distillation residue which contained the catalyst was again reused as above with another 100 g. of d-limonenen and after 24 hours the reaction mixture was distilled providing product containing 60% 3-menthene, 12% 1-menthene, 5% limonene, 11% 4(8)-menthene and 8% terpinolene and 2,4(8)-menthadiene.

EXAMPLE 6

A procedure very similar to that described in Example 1 was employed using 42.2 g. d-limonene. 0.05 g. RuCl$_2$(CO)$_2$(PPh$_3$)$_2$ catalyst, 20 ml. solvent, and in some cases, a small amount of added triphenylphosphine. The solvent used in each run and the results obtained are given below.

TABLE 3

| Run No | Solvent | Ph$_3$P(g) | Time (Hrs.) | Temp (°C.) | Hydrogen Press (psig) | % 3-Menthene | % 1-Menthene | % Limonene |
|---|---|---|---|---|---|---|---|---|
| 1 | Toluene | 0 | 4 | 140 | 400 | nil | 76 | 6 |
| 2 | Toluene | 1.0 | 22 | 140 | 200 | 2 | 29 | 50 |
| 3 | Ethanol | 1.0 | 21 | 160 | 400 | 3 | 39 | 21 |
| 4 | Toluene | 2.0 | 23 | 140 | 400 | 2.2 | 22 | 62 |

These results show that the selective hydrogenation of d-limonene to 3-menthene did not occur to an appreciable extent under the reacton conditions utilized in the reported runs. It is possible that a combination of conditions could be developed which would result in improved selectivities of 3-menthene formation (eg. use of DMF as reported in Examples 1 and 7 or use of other amide or lactam solvent). Accordingly, the use of solvents reported above with limonene are considered to be within the purview of the present invention.

EXAMPLE 7

A series of runs was carried out using toluene as a solvent in order to determine the effect of reducing the amount of DMF used. In each run, 10 g. of limonene was subjected to hydrogenation at 160° C. under a pressure of 100–140 psig. with 0.01 g. RuCl$_2$(CO)$_2$(PPh$_3$)$_2$ catalyst for 8 hours. The following table summarizes the results.

TABLE 4

| No. Run | Tolene (g.) | DMF, (g.) | φ$_3$P (g.) | % Conversion | % 3-Menthene | 3-Methene: 1-Menthene (wt. ratio) |
|---|---|---|---|---|---|---|
| 1 | 5 | 2 | — | 98 | 60 | 3.2 |
| 2 | 5 | 1 | — | 98 | 58 | 2.9 |
| 3 | 5 | 0.5 | — | 62 | 42 | 1.1 |
| 4 | 5 | 0 | — | 36 | 12 | * |
| 5 | 5 | 1 | .03 | 88 | 42 | 2.4 |
| 6 | 5 | 0 | .03 | 73 | 16 | 0.5 |

*Separation of 1-menthene and limonene was not complete enough for computer integration.

The foregoing results show that excellent conversions of feed limonene to products and excellent yields of the desired 3-menthene in such products can be achieved by the use of a combination of an organic solvent and an amide solvent.

EXAMPLE 8

Mixtures of terpinolene and 2,4(8)-methadiene were selectively hydrogenated to 3-menthene in the presence of RuCl$_2$(CO)$_2$(PPh$_3$)$_2$ catalyst complex. Details of the reactions and results obtained are as follows:

TABLE 5a

| REACTION CONDITIONS | | | | | |
|---|---|---|---|---|---|
| Run No. | Menthadienes (wt-%) | Solvent | Temp (°C.) | Pressue (psig) | Catalyst Complex (wt-%) |
| 1 | 26.71% terpinolene 67.71% 2,4(8)-Menthadien | Toluene | 140 | 360–400 | 0.125 |
| 2 | 89.51% terpinolene 7.50% 2,4(8)-Menthadiene | Toluene | 150–160 | 350–400 | 0.143 |

TABLE 5

| RESULTS | | | | | |
|---|---|---|---|---|---|
| Run No. | Tome (hrs) | 3-Menthene (wt-%) | 1-Menthene & 4(8)-Menthene (wt-%) | Terpinolene (wt-%) | 2,4(8)-Menthadiene (wt-%) |
| 1 | 4 | 9.44 | 2.92 | 19.80 | 62.80 |
|   | 22 | 44.55 | 13.83 | 5.72 | 33.82 |
|   | 54 | 71.42 | 25.46 | nil | 2.65 |
| 2 | 4 | 4.92 | 1.74 | 56.53 | 34.49 |
|   | 23 | 41.83 | 12.55 | 8.74 | 33.64 |
|   | 65 | 65.78 | 28.38 | 0.77 | 0.55 |

Again, a highly selective hydrogenation process is demonstrated.

EXAMPLE 9

Citrus d-limonene (10 g.) was stirred at 160° C. in the presence of dimethylacetamide (5 ml.) and RuCl$_2$(CO)$_2$(PPH$_3$)$_2$(0.1 gm.), under a hydrogen pressure of 40–100 psig. Sampling after 6 hours reaction time showed complete conversion of limonene and production of 55.2% 3-methene and 23.6% 1-menthene.

EXAMPLE 10

The procedure of Example 9 was repeated except that dimethylacetamide was replaced with N-methylpyrrolidone (5 ml.) Again, sampling after 6 hours reaction time showed complete conversion of limonene, and production of 54.5% 3-menthene and 23.1% 1-menthene.

EXAMPLE 11

Isolimonene (100 g.) obtained by pyrolysis of optically active 2-carene was stirred at 140° C. in the presence of dimethylformamide (50 ml.) and RuCl$_2$ (CO)$_2$(PPh$_3$)$_2$(1.0 g.) and under a hydrogen pressure of 130–200 psig. Periodic sampling and analysis by vapor phase chromatography gave the following results:

TABLE 6(a)

| Sample Time | % Iso-limonene | % 3-Menthene | % 1-Menthene | % Limonene | % 4(8)-Menthene | % Terpinolene + 2,4(8)-Menthadiene |
|---|---|---|---|---|---|---|
| 2 hr. | 9.35 | 47.85 | 8.48 | 5.98 | 12.05 | 8.58 |
| 6 hr. | 6.37 | 54.93 | 19.07 | — | 14.13 | trace |

After cooling, the layers were separated and the lower layer containing catalyst was stirred with 70.8 g. of isolimonene under similar conditions. Periodic sampling gave the following results:

TABLE 6(b)

| Sample Time | % Iso-limonene | % 3-Menthene | % 1-Menthene | % Limonene | % 4(8)-Menthene | 2,4(8)-Menthadiene |
|---|---|---|---|---|---|---|
| 6 hr. | 10.72 | 49.35 | 21.39 | — | 11.89 | trace |
| 10 hr. | 13.59 | 45.15 | 23.15 | — | 10.18 | trace |

The products from the two runs were combined and subjected to distillation at reduced pressure to provide pure 3-menthene. The optical purity of the 3-menthene was determined to be 49% by conversion to the enol acetate of menthone.

We claim:

1. A process for catalytically hydrogenating a nonconjugated paramenthadiene having one site of unsaturation at the 4(8)-or the 8-position, for selectively forming 3-menthene which comprises:

contacting with hydrogen gas under hydrogenation conditions a reaction mixture comprising said paramenthadiene, a catalytic proportion of a ruthenium (II) catalyst complex, and an organic solvent in which said catalyst complex is homogeneously dispersed, until said 3-menthene is formed, said catalyst complex restricted to one which is capable of catalyzing a selective hydrogenation of a cyclic polyene to a cyclic monoene.

2. The process of claim 1 wherein said catalyst complex is of the formula $$RuX_2(CO)_a(L)_b,$$

where
X is a halogen or a hydrogen atom,
a is 0, 1, or 2
b is 2 or 3,
a+b is 3 or 4
L is $PR_3$ or $R_2P—R'—PR_2,$ where R is an alkyl, aryl, cycloalkyl radical or combinations thereof, and R' is an alkylene or cycloalkylene radical.

3. The process of claim 2 wherein said catalyst complex is $RuCl_2(CO)_2 (Ph_3P)_2$, wherein Ph is a phenyl group.

4. The process of claim 1 wherein said para-menthadiene is selected from limonene, terpinolene, isolimonene, psi-limonene, 1(7), 4(8)-menthadiene, and mixtures thereof, provided that when said para-menthadiene is limonene that said solvent comprises an amide or lactam solvent.

5. The process of claim 1 wherein said solvent comprises an amide or lactam solvent.

6. The process of claim 2 wherein said solvent comprises an amide or lactam solvent.

7. The process of claim 6 wherein said solvent comprises dimethylformamide.

8. The process of claim 3 wherein said solvent comprises dimethylformamide and an organic co-solvent.

9. The process of claim 8 wherein said organic co-solvent is an aromatic solvent.

10. The process of claim 2 wherein the proportion of said catalyst complex in said reaction mixture is between about 0.05% and 100% by weight.

* * * * *